United States Patent [19]

Schwartzkopf

[11] Patent Number: 4,752,551
[45] Date of Patent: Jun. 21, 1988

[54] PHOTOSENSITIVE SOLUBILIZATION INHIBITION AGENTS, AND DEEP ULTRA-VIOLET LITHOGRAPHIC RESIST COMPOSITIONS

[75] Inventor: George Schwartzkopf, Franklin Township, Warren County, N.J.

[73] Assignee: J. T. Baker Inc., Phillipsburg, N.J.

[21] Appl. No.: 914,473

[22] Filed: Oct. 2, 1986

[51] Int. Cl.$^4$ .................. G03C 1/54; G03C 1/60; C07C 113/00
[52] U.S. Cl. .................. 430/191; 430/170; 430/192; 430/193; 430/326; 430/330; 534/556
[58] Field of Search ............... 430/170, 193, 192, 191; 534/556

[56] References Cited

U.S. PATENT DOCUMENTS

| | | | |
|---|---|---|---|
| 4,339,522 | 7/1982 | Balanson et al. | 430/192 |
| 4,522,911 | 6/1985 | Clecak et al. | 430/193 |
| 4,622,283 | 11/1986 | Gray | 430/193 |
| 4,624,908 | 11/1986 | Schwartzkopf | 430/193 |
| 4,626,491 | 12/1986 | Gray | 430/190 |

OTHER PUBLICATIONS

Schwall, H., et al, "Thermolysis of 6-Membered 2-Diazo-1,3 Diketones in Pyridine and in Aniline", *Index Chemicals*, 34, 115474, (1969).
Best, W. M., et al., "Intramolecular Diels–Alder Additions of Benzynes to Furans", *Current Abstracts of Chemistry*, vol. 103, Issue 1189, 1986.
Korobitsyna, I. K., et al., *Zhurnal Organicheskoi Khimii*, Jun. 1976, vol. 12, No. 6, pp. 1245–1260.

Deep UV Photoresists I. Meldrum's Diazo Sensitizer, Barbara D. Grant et al.
IEEE Transactions on Electron Devices, vol. ED-28, No. 11, Nov. 1981.

*Primary Examiner*—Charles L. Bowers, Jr.
*Attorney, Agent, or Firm*—Parmelee, Bollinger & Bramblett

[57] ABSTRACT

Photosensitive solubilization inhibitor compounds of the formula

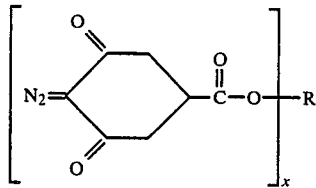

wherein:
x is an integer equal to the valence or functionality of the radical R, and
R is a radical selected from the group consisting of the residue of a mono-, di-, tri- or polyfunctional alkanol or silicon-containing alkanol and is attached to the oxy atom of the carboxyl group through a carbon atom.

Positive deep ultra-violet photoresists which are base developable comprise base soluble polymers and the photosensitive solubilization inhibition agents. Lithographic resist images are formed with the deep ultra-violet photoresists upon exposure to deep ultra-violet light.

31 Claims, 3 Drawing Sheets

PHOTOSENSITIVE SOLUBILIZATION INHIBITION AGENTS, AND DEEP ULTRA-VIOLET LITHOGRAPHIC RESIST COMPOSITIONS

FIELD OF THE INVENTION

This invention relates to deep ultra-violet photosensitive solubilization inhibition agents, photoresists compositions containing a resin and said photosensitive solubilization inhibition agents and to a process for forming a lithographic resist image employing said photoresist compositions.

BACKGROUND OF THE INVENTION

Due to the advancing state of the art in the projection or lithographic printing field, it has become highly desirable to be able to provide image geometries of less than 2 microns and very high device packing densities. In order to most advantageously obtain same, it has become highly desirable that projection imaging wavelengths in the deep ultra-violet (UV) region of below about 300 nm be employed. It is therefore desirable that suitable deep UV resist compositions be available for use with imaging wavelengths in the deep UV region.

Recently U.S. Pat. No. 4,339,522 to R. Balamson et al., issued July 13, 1982 and assigned to International Business Machines Corporation, disclosed such a deep UV resist composition which comprises phenolic-aldehyde resins sensitized with Meldrum's acid diazo or a homologue thereof as a dissolution rate inhibitor for the matrix resin in the unexposed imaging layer. In the exposed regions the inhibition agent undergoes a radiation induced structural transformation which alters its efficiency as a dissolution rate inhibitor for the matrix resin. Thus, the exposed regions are rendered more soluble than the unexposed regions and the difference in solubility rates is utilized to generate the positive lithographic patterns.

However, such sensitizers such as Meldrum's acid diazo and homologues thereof suffer from a lack of thermal stability and undue volatility. As a result there is often a substantial loss of such sensitizing agents during wafer prebake. As a result the sensitizing agent is not completely retained in the photoresist layer and lower prebake temperatures have had to be employed. Another undesirable result has been the fact that the wall profiles of the resist images are somewhat undercut.

The loss of sensitizer that occurs during prebake also results in process variability and inhibit reproducible wafer performance. Also, the UV dosage required to achieve good image quality and useful processing is undesirably high.

Therefore, a need exists for deep UV photosensitive solubilization inhibitors for use in deep UV photoresist compositions which inhibitors possess improved thermal stability, lower volatility and have improved retention in the photoresist composition during prebake operations. Moreover, it is also highly desirable that such inhibitors be able to endure higher prebake temperatures without loss of retention in the photoresist compositions.

Additionally, it is most desirable that such solubilization inhibition agents be available which provide deep UV photoresist compositions having higher lithographic photosensitivity and allowing for usage of lower UV dosages in processing. Another desirable feature would be such solubilization inhibitors that allow for shorter clearing or developing times yet with higher sensitivity. Especially desirable would be the availability of such solubilization inhibitors producing deep UV resist compositions providing good resolution of 0.75 micron lines or smaller.

SUMMARY OF THE INVENTION

Positive deep UV photoresists which are sensitive to light in the deep UV range of from about 240–300 nm and which are base soluble are provided by resists comprising a base soluble polymer and novel 4-diazo-3,5-dioxocyclohexane carboxylic acid ester photosensitive solubilization inhibition agents selected from the group consisting of compounds of the formula

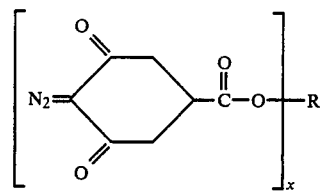

wherein:

x is an integer equal to the valence or functionality of the radical R, and

R is a radical selected from the group consisting of the residue of a mono-, di-, tri- or polyfunctional alkanol or silicon-containing alkanol and is attached to the oxy atom of the carboxyl group through a carbon atom.

DETAILED DESCRIPTION OF THE INVENTION

Figure 1:
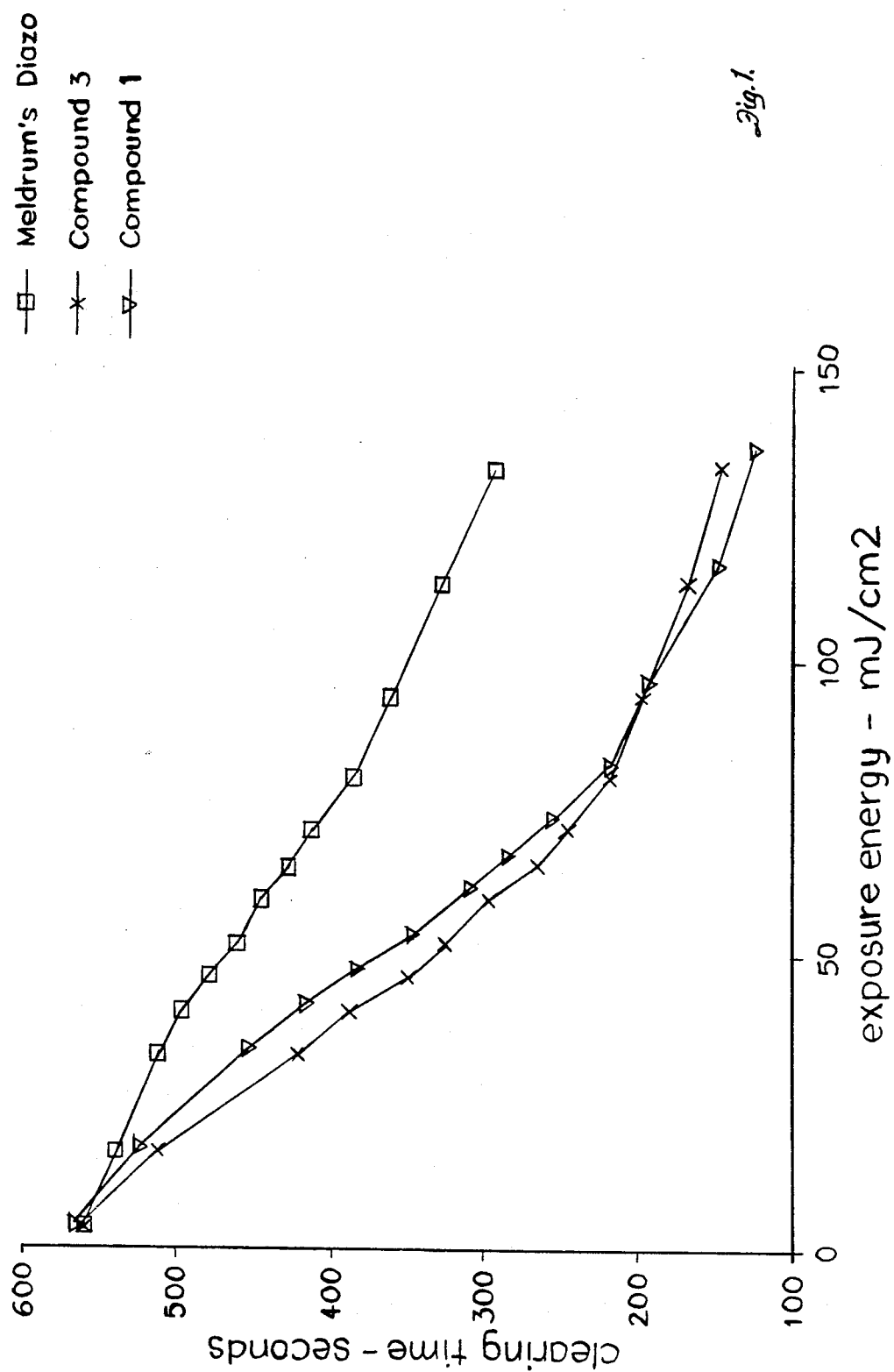
FIGS. 1, 2 and 3 are plots of photoresist clearing times in seconds versus exposure energy in mJ/cm$^2$ for compounds of this invention and for the prior art Meldrum's diazo compound.

In the above formula x is preferably 1 to about 3 and R is preferably the residue of a mono-, di- or tri-functional alkanol or silicon-containing alkanol having from about 1 to about 20 carbon atoms, more preferably from 2 to about 6 carbon atoms and most preferably about 6 carbon atoms. The alkanol residue may be either a straight or a branched chain.

As examples of R radicals there may be mentioned for example, methyl, ethyl, propyl, isopropyl, butyl, t-butyl, amyl, hexyl, decyl, eicosyl and the like and corresponding radicals where one or more of the carbon atoms is replaced by a silicon atom.

Preferred as solubilization inhibition agents of this invention are compounds of the Formula in which x is 1 to 3 and in which R is the residue of the following alkanols:

ethanol
2-trimethylsilylethanol
2-ethyl-2-methyl-1,3-propanediol
1,6-hexanediol
3,3-dimethyl-3-silapentane-1,5-diol, and
trimethylolpropane.

The compounds useful as solubilization inhibition agents according to this invention can be easily prepared, for example, by esterifying 3,5-dioxocyclohexane carboxylic acid with the alkanol according to known esterification procedures and converting the resulting 3,5-dioxocyclohexane carboxylic acid ester to the corresponding 4-diazo-3,5-dioxocyclohexane carboxylic acid ester by reacting the ester with any suitable sulfonylazide, such as p-toluenesulfonyl azide (TSA) or naphthylenesulfonyl azide (NSA), in the presence of a catalyst such as dry triethylamine and any suitable solvent such as ethanol, benzene or acetonitrile any the like. Generally after reacting for a period of about 3 to about 15 hours the reaction mixture is filtered to remove the precipitated sulfonamide and the filtrate is evaporated to dryness. The product may then be partially purified by partitioning between methylene chloride and dilute alkali hydroxide. The residues may be purified either by recrystallization, if the product is a solid, or by chromatography, such as flash chromatography on silica gel if the product is an oil.

Exemplary of the preparation of compounds of the Formula for use as solubilization inhibition agents according to the invention are the following Examples 1-5.

EXAMPLE 1

2-(Trimethylsilylethyl)-4-Diazo-3,5-Dioxocyclohexane carboxylate

A mixture of 3.00 g (19.2 mmole) 3,5-dioxocyclohexane carboxylic acid (M. E. Kuehne and B. F. Lambert, J. Am. Chem. Soc., 81, 4278 (1959)), 2.27 g (19.2 mmole) of 2-trimethylsilylethanol (Petrarch Systems, Inc.) and 0.23 g (1.9 mmole) 4-dimethylaminopyridine in 120 mL methylene chloride was stirred at room temperature and treated dropwise with 4.36 g (21.1 mmole) of dicyclohexylcarbodiimide dissolved in 90 mL of methylene chloride. After stirring overnight the mixture was filtered and the filtrate washed with 1N $KHSO_4$ (aqueous) and dried over $Na_2SO_4$. The dried extract was concentrated in vacuo and the crude product dissolved in 50 mL of benzene, then 200 mL of petroleum ether was added to precipitate the desired intermediate, 2-(trimethylsilyethyl)-3,5-dioxocyclohexanecarboxylate (2.24 g).

This material (8.75 mmole) was dissolved in 25 mL benzene and 25 mL acetonitrile and cooled in an ice bath. The stirred cold solution was treated with 1.28 mL (9.18 mmole) triethylamine followed by 1.90 g (9.6 mmole) of p-toluenesulfonyl azide (M. Regitz, et al., Organic Synthesis, Coll. Vol. 5, John Willey & Sons (1973) p. 179). The ice bath was removed after one hour and stirring continued overnight. The reaction mixture was concentrated in vacuo at 40° C. and the residue dissolved in methylene chloride and washed with 1N NaOH (aqueous) and dried over $Na_2SO_4$. Concentration gave 2.08 g crude product. This was chromatographed on 40 micron silica gel giving 1.12 g of 2-(Trimethylsilylethyl)-4-Diazo-3,5-Dioxocyclohexane carboxylate as an amber oil. Elemental analysis calculated for $C_{12}H_8N_2O_4Si$: C, 51.04; H, 6.42; N, 9.92. Found: C, 51.10; H, 6.47; N, 9,86. Satisfactory pmr, cmr, ir, and uv spectra were obtained.

EXAMPLE 2

2,2-Bis-(4-Diazo-3,5-Dioxocyclohexane-1-Carbonyloxy methyl)Butane

The preparation was similar to Example 1 but using 1.14 g (9.65 mmoles) of 2-ethyl-2-methyl-1,3-propanediol as the alcohol component. Esterification and diazo transfer as described in Example 1 gave 0.53 g of 2,2-Bis-4-Diazo-3,5-Dioxocyclohexane-1-Carbonyloxy methyl)-Butane as an amber oil. Elemental analysis - calculated for $C_{20}H_{22}N_4O_8$: C, 53.81; H, 4.97; N, 12.55. Found: C, 53.63; H, 5.07; N, 12.54. Satisfactory pmr, cmr, ir and uv spectra were obtained.

EXAMPLE 3

1,6-Bis-(4-Diazo-3,5-Dioxocyclohexane-1-Carbonyloxy)-Hexane

The preparation was similar to Example 1 but using 1.14 g (9.65 mmoles) of 1,6-hexandiol as the alcohol component. Esterification and diazo transfer as described in Example 1 gave 0.72 g of Compound 1,6-Bis-(4-Diazo-3,5-Dioxocyclohexane-1-Carbonyloxy)-Hexane. Satisfactory pmr, cmr, ir and uv spectra were obtained.

EXAMPLE 4

1,5-Bis-(4-Diazo-3,5-Dioxocyclohexane-1-Carbonyloxy)-3,3-Dimethyl-3-Silapentane

The preparation was similar to Example 1 but using 1.42 g (9.59 mmoles) of 3,3-dimethyl-3-silapentane-1,5-diol (J. A. Sonderquist, et al., J. Org. Chem. 49, 2565 (1984)) as the alcohol component. Esterification and diazo transfer as described in Example 1 gave 0.62 g of 1,5-Bis-(4-Diazo-3,5-Dioxocyclohexane-1-Carbonyloxy)-3,3-Dimethyl-3-Silapentane as a pale yellow oil. Elemetal analysis - calculated for $C_{20}H_{24}N_4O_8Si$: C, 50.41; H, 5.08; N, 11.76. Found: C, 5055, H, 4.90; N, 11.98. Satisfactory pmr, cmr, ir and uv spectra were obtained.

EXAMPLE 5

1,1,1-Tris-(4-Diazo-3,5-Dioxocyclohexane-1-Carbonyloxy methyl) Propane

The preparation was similar to Example 1 but using 0.86 g of trimethylolpropane (6.4 mmoles) as the alcohol component. Esterification and diazo transfer as described in Example 1 gave 0.83 g of 1,1,1-Tris-(4-Diazo-3,5-Dioxocyclohexane-1-Carbonyloxy methyl)-Propane as an amorphous solid. Satisfactory pmr, cmr, ir and uv spectra were obtained.

When the solubilization inhibition agents of this invention are added to base soluble acidic polymers and the resulting photoresist compositions are cast as films on substrates the solubilization inhibition agents inhibit the solubility of the polymeric film in developer in the area of the film which has not been exposed to the deep UV light compared to the area of the polymeric film exposed to UV light.

Any suitable base soluble acidic photoresist polymer can be employed in the photoresist compositions of this invention, such as the commercially available phenol-formaldehyde resins, cresol-formaldehyde resins, poly(-vinylphenol), and copolymers of methacrylic acid with esters thereof, such as, poly(methyl methacrylate-methacrylic acid) resins and the like. A particularly preferred resin is a poly(methyl methacrylate-methacrylic acid) resin having a methacrylic acid content of between about 20 to 30%, preferably about 25% by weight, having a molecular weight (by gel permeation chromatography) of between about 20,000 to 120,000, preferably about 80,000, and having a narrow polydispersity. Such a resin is one prepared according to the following method. A solution of 4.9 liters of the appropriate amounts of methyl methacrylate and methacrylic acid (a total of 17.5 moles of the two monomers) is stirred under $N_2$ at 80°±2° C. as 300 ml aliquots of a solution of the appropriate amount of 2,2-diazo bis (2-methylpropionitrile) (3.5 g for a polymer with a molecular weight of 80,000 or 16.5 for a polymer with a molecular weight of 20,000) in 2100 ml of 1,2-dimethoxyethane were added at 30 min. intervals. When the addition is completed, the reaction mixture is stirred at 80°±2° C. for an additional 16 hours before being evaporated to dryness. The residue is washed with 15 liters of dichloromethane for 24 hours and then the wash is decanted and discarded. The insolubl polymer is dissolved in 15 liters of methanol and the solution is filtered. The filtrate is evaporated to dryness to yield the polymeric product.

The photoresist compositions of this invention comprise about 50 to 95% by weight base soluble polymer and from about 5 to about 50% by weight of a solubilization inhibition agent of this invention, preferably about 70% base soluble polymer and about 30% solubilization inhibition agent. The resists may be formed readily by dissolving the polymer and solubilization inhibition agent in a common solvent and casting a film onto an appropriate substrate. Any suitable film-forming solvent may be used, generally film-forming solvents having a boiling point of from about 120 to 210° C, such as for example, diglyme, methyl isobutyl ketone, 2-methoxyethanol, 2-ethoxyethanol, 2-methoxyethyl acetate, γ-butyrolactone and the like. The resist forming composition will generally comprise from about 50 to about 95% by weight solvent and about 5 to about 50% by weight solid (i.e. base soluble polymer and solubilization inhibition agent combined). Preferably the solvent will comprise about 80 to 90% by weight and the solids about 10 to 20% by weight. The amount of solids employed will be dependent upon the desired viscosity of the resist forming composition and is such as permits the casting of a resist of about 1 micron thick.

The solubilization inhibition agents of this invention possess improved thermal stability and lower volatility compared to compounds previously proposed for such use. When incorporated into castable resist compositions with film-forming polymer and an appropriate film-forming solvent and subject to pre-baking to set the photoresist on the substrate, the lower volatility of these solubilization inhibition agents results in cured photoresist with less loss of solubilization inhibition agent thereby leading to an improved solubility differential between exposed and unexposed photoresist.

Solutions of the solubilization inhibition agents of Examples 1 to 5, as well as Meldrum's diazo of U.S. Pat. No. 4,339,522 and 2-diazo-5,5-dimethylcyclohexane-1,3-dione (0.55 g in 12.1 g of a 10.6% solution of poly(methylmethacrylate)copoly(methacrylic acid) (3:1) in 2-methoxyethanol) were each spun onto quartz wafers at 2500 RPM to produce high quality films about a micron thick. The UV absorbance at the diazo maximum wavelength (approximately 260 nm) was measured on the film using a matched quartz wafer as the blank. The wafers were then subject to baking at temperatures of 79° C. and 92.5° C. for 30 minutes and the UV absorbance was again measured on the film using matched quartz wafer as the blank.

From these two UV absorbance measurements the percent solubilization inhibition agent remaining in the wafer was calculated by use of the equation $$\% \text{ agent remaining} = \frac{\text{absorbance after baking}}{\text{absorbance before baking}} \times 100.$$

Data for the compounds of this invention and for the two comparative compounds is set forth in the following Table:

| Compound | Bake Temperature °C. | % Compound Remaining |
|---|---|---|
| Example 1 | 79 | 81 |
| Example 2 | 79 | 100 |
|  | 92.5 | 98 |
| Example 3 | 92.5 | 98 |
| Example 4 | 79 | 100 |
|  | 92.5 | 98 |
| Example 5 | 79 | 99 |
|  | 92.5 | 98 |
| Meldrum's diazo | 79 | 65 |
| 2-diazo-5,5-dimethyl-cyclohexane-1,3-dione | 79 | 64 |

The comparison demonstrates that much more of the compounds of this invention are retained (i.e. much less is lost) from the photoresist layers during prebake than the compounds of the prior art. This is due to the lower volatility and higher thermal stability of the new compounds. This permits the solubilization inhibition agents of this invention to be used at higher prebake temperatures as well as eliminating or substantially reducing any process variability that would be introduced by the use of the less stable and more volatile prior art compounds.

The lithographic sensitivities of the compounds of Examples 1 to 4 were compared with that of Meldrum's diazo by comparing the clearing times at various imaging dosages using developer conditions that gave approximately equal clearing times for unexposed films.

Solutions of the solubilization inhibition agents of Examples 1 to 4 as well as Meldrum's diazo (0.55 g in 12.1 g of a 10.6% solution of poly(methylmethacrylate)-copoly(methacrylic acid) (3:1) in 2-methoxyethanol) were spun onto silicon wafers. Spinning speeds were adjusted so that wafers to be compared had similar resist film thicknesses.

The coated wafers were prebaked at the following temperatures: 78° C. for the compounds of Examples 1, 2 and Meldrum's diazo, 92.5° C. for the compound of Example 4 and 110° C. for the compound of Example 3. The prebaked wafers were then exposed to deep UV radiation using a high-pressure mercury-xenon lamp and a deep UV filter transmitting from 240-300 nm through a quartz multidensity mask giving a series of fifteen exposures on each photoresist film. The photoresist layers were then developed using aqueous triethanolamine and the clearing time for each exposure measured using a development rate monitor. The pH and temperature of the developer solutions were adjusted so that photoresist layers to be compared had approximately equal clearing times for unexposed areas.

Figure 2:
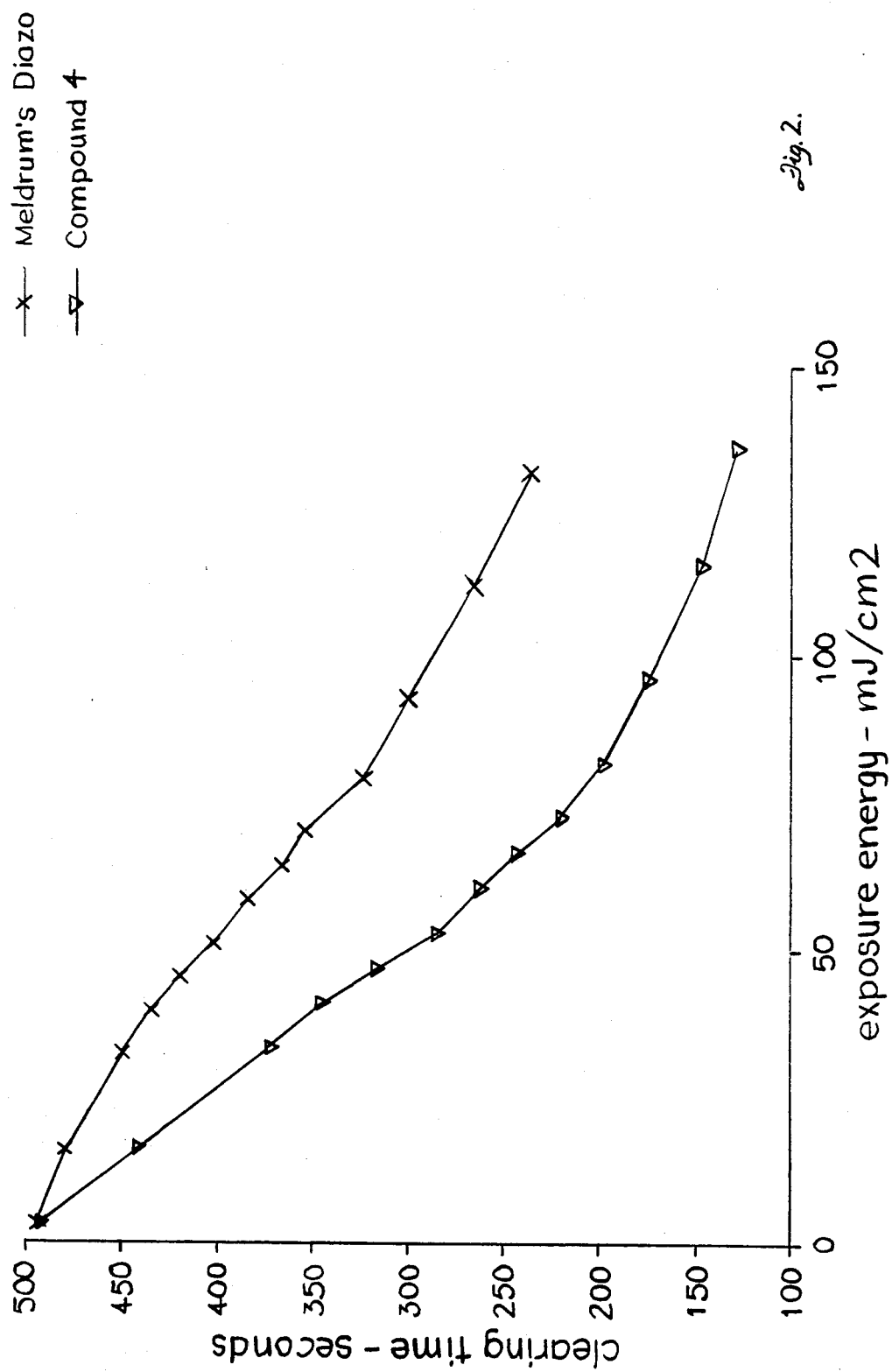
Figure 3:
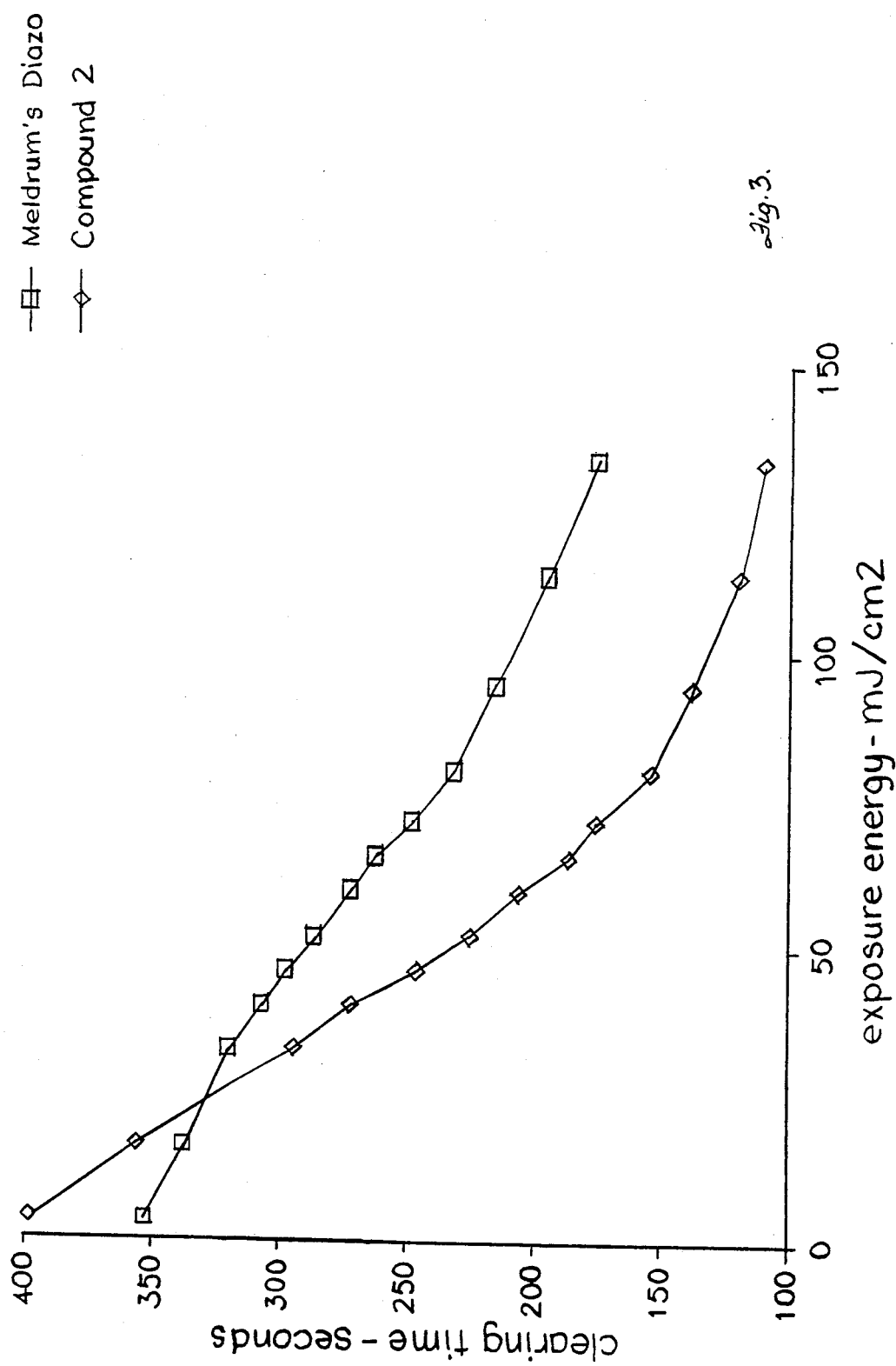

The clearing time data is depicted in FIGS. 1 to 3 where clearing time is plotted versus exposure energy for the various compounds employed. In each case the clearing times of the compounds of this invention are approximately one-half those of the prior art Meldrum's diazo compound at the usable dosage of about 100 mJ/cm$^2$ (broadband 260 nm radiometer). This reflects the approximate double lithographic photosensitivity of the compounds of this invention compared to the prior art and allows their use at lower deep UV radiation doses. Moreover, the compounds of Examples 3 and 4 are demonstrated to remain quite photosentive even though higher prebake temperatures were employed.

This sensitivity data was also treated quantitatively using the method described by C. G. Wilson, Introduction to Microlithography, ACS Symposium Series, No. 219, pp 99–105, American Chemical Society, 1983. A comparative sensitivity dose, $D_s$, was calculated for each of the films compared in FIGS. 1 to 3. Results are shown below:

| FIG. NO. | Compound | Ds |
|---|---|---|
| 1 | Meldrum's diazo | 465 |
|   | Example 3 | 117 |
|   | Example 1 | 136 |
| 2 | Meldrum's diazo | 318 |
|   | Example 4 | 166 |
| 3 | Meldrum's diazo | 282 |
|   | Example 2 | 158 |

In each comparison the sensitivity dose for Meldrum's diazo was about 2 times as great or more than the sensitivity dose for the compounds of the invention.

A solution of 0.55 g of the compound of Example 4 in 12.1 g of a 10.6% solution of poly(methyl-methacrylate)copoly(methacrylic acid) (3:1) in 2-methoxyethanol) produced high-quality films 1 micron thick when spun at 2500 RPM. No loss of sensitizer was observed on baking these films at 92° C. for 30 minutes prior to exposure. The use of a deep UV radiation dose of approximately 100 mJ/cm$^2$ (broadband 260 nm radiometer) gives an irradiated region that is developed to substrate with little film loss from the unexposed portion using 0.4% aqueous triethanolamine developer. Using similar conditions, submicron geometries were resolved using a Perkin-Elmer Micralign 500 projection aligner in the UV II mode to expose the resist coated wafers.

What is claimed is:

1. A 4-diazo-3,5-dioxocyclohexane carboxylic acid ester of the formula:

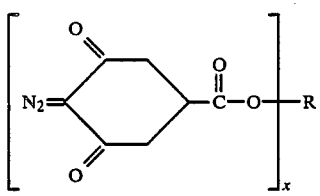

wherein
x is an integer of from 1 to 3 and equal to the valence or functionality of the radical R, and
R is a radical selected from the group consisting of the residue of a mono-, di- or tri- functional alkanol or silicon-containing alkanol and is attached to the oxy atom of the carboxyl group through a carbon atom.

2. A compound of claim 1 wherein the R radical contains from 1 to about 20 carbon atoms.

3. A compound of claim 2 wherein the R radical contains from about 2 to about 6 carbon atoms.

4. A compound of claim 1 which is 2-(trimethylsilylethyl)-4-diazo-3,5-dioxocyclohexanecarboxylate.

5. A compound of claim 1, which is 2,2-bis-(4diazo-3,5-dioxocyclohexane-1-carbonyloxy methyl)butane.

6. A compound of claim 1, which is 1,6-bis-(4-diazo-3,5-dioxocyclohexane-1-carbonyloxy)-hexane.

7. A compound of claim 1, which is 1,5-bis-(4-diazo-3,5-dioxocyclohexane-1-carbonyloxy)-3,3-dimethyl-3-silapentane.

8. A compound of claim 1, which is 1,1,1-tris-(4-diazo-3,5-dioxocyclohexane-1-carbonyloxy methyl)propane.

9. A lithographic resist composition for use with deep UV light of less than 300 nm comprising a base soluble film-forming polymer and in admixture therewith a photosensitive solubilization inhibiting amount of a photosensitive solubilization inhibition agent which is a 4-diazo-3,5-dioxocyclohexane carboxylic acid ester compound of the formula:

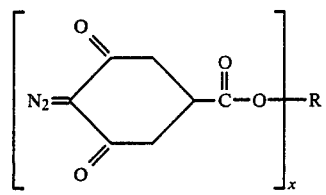

wherein:
x is an integer of from 1 to 3 equal to the valence or functionality of the radical R, and
R is a radical selected from the group consisting of the residue of a mono-, di- or tri- functional alkanol or silicon-containing alkanol and is attached to the oxy atom of the carboxyl group through a carbon atom, whereby upon exposure to deep UV radiation the exposed composition becomes more soluble in alkaline developer.

10. A resist composition of claim 9 wherein the base soluble film-forming polymer is a resin selected from the group consisting of phenol-formaldehyde, cresol-formaldehyde, poly(vinylphenol) and poly(methyl methacrylate-methacrylic acid) resins.

11. A resist composition of claim 9 wherein the solubilizing agent is present in an amount of from about 5 to about 50% by weight based on the combined weight of polymer and agent.

12. A resist composition of claim 11 wherein the R radical contains from 1 to about 20 carbon atoms.

13. A resist composition of claim 12 wherein the R radical contains from about 2 to about 6 carbon atoms.

14. A resist composition of claim 11 wherein the ester compound is 2-(trimethylsilylethyl)-4-diazo-3,5-dioxocyclohexane-carboxylate.

15. A resist composition of claim 11 wherein the ester compound is 2,2-bis-(4-diazo-3,5-dioxocyclohexane-1-carbonyloxy methyl)-butane.

16. A resist composition of claim 11 wherein the ester compound is 1,6-bis-(4-diazo-3,5-dioxocyclohexane-1-carbonyloxy)-hexane.

17. A resist composition of claim 11 wherein the ester compound is 1,5-bis-(4-diazo-3,5-dioxocyclohexane-1-carbonyloxy)-3,3-dimethyl-3-silapentane.

18. A resist composition of claim 11 wherein the ester compound is 1,1,1-tris-(4-diazo-3,5-dioxocyclohexane-1-carbonyloxy methyl)propane.

19. A resist composition of claim 11 wherein the polymer is a poly (methyl methacrylate-methacrylic acid).

20. A resist composition of claim 19 wherein the poly(methyl methacrylate-methacrylic acid) has a molecular weight of about 80,000 and the ratio of methacrylate to methacrylic acid is 75/25.

21. A castable resist composition comprising the lithographic resist composition of claim 9 in a film-forming solvent having a boiling point of from about 120° to 210° C.

22. A castable resist composition of claim 21 wherein the solvent comprises from about 50 to about 95% by weight of the castable composition.

23. A castable resist composition of claim 22 wherein the solvent is selected from the group consisting of diglyme, methyl isobutyl ketone, 2-methoxyethanol, 2-ethoxyethanol, 2-methoxyethyl acetate and γ-butyrolactone.

24. A castable resist composition comprising the lithographic resist composition of claim 11 in a film-forming solvent having a boiling point of from about 120° to 210° C.

25. A castable resist composition comprising the lithographic resist composition of claim 12 in a film-forming solvent having a boiling point of from about 120° to 210° C.

26. A castable resist composition comprising the lithographic resist composition of claim 13 in a film-forming solvent having a boiling point of from about 120° to 210° C.

27. A castable resist composition comprising the lithographic resist composition of claim 14 in a film-forming solvent having a boiling point of from about 120° to 210° C.

28. A castable resist composition comprising the lithographic resist composition of claim 15 in a film-forming solvent having a boiling point of from about 120° to 210° C.

29. A castable resist composition comprising the lithographic resist composition of claim 16 in a film-forming solvent having a boiling point of from about 120° to 210° C.

30. A castable resist composition comprising the lithographic resist composition of claim 17 in a film-forming solvent having a boiling point of from about 120° to 210° C.

31. A castable resist composition comprising the lithographic resist composition of claim 18 in a film-forming solvent having a boiling point of from about 120° to 210° C.

* * * * *